(12) United States Patent
Blum

(10) Patent No.: US 9,642,981 B2
(45) Date of Patent: May 9, 2017

(54) SYSTEMS AND METHODS OF PREPARING A CONTROLLED MIXTURE FOR HYPERTHERMAL TREATMENT

(71) Applicant: Michael Blum, New York, NY (US)

(72) Inventor: Michael Blum, New York, NY (US)

( * ) Notice: Subject to any disclaimer, the term of this patent is extended or adjusted under 35 U.S.C. 154(b) by 0 days.

(21) Appl. No.: 14/386,400

(22) PCT Filed: Mar. 23, 2013

(86) PCT No.: PCT/IB2013/052317
§ 371 (c)(1),
(2) Date: Sep. 19, 2014

(87) PCT Pub. No.: WO2013/144806
PCT Pub. Date: Oct. 3, 2013

(65) Prior Publication Data
US 2015/0040902 A1    Feb. 12, 2015

(30) Foreign Application Priority Data

Mar. 24, 2012 (GB) .................................. 1205196.7

(51) Int. Cl.
*A61M 16/16* (2006.01)
*A61M 16/00* (2006.01)
(Continued)

(52) U.S. Cl.
CPC .......... *A61M 16/16* (2013.01); *A61M 11/042* (2014.02); *A61M 11/044* (2014.02);
(Continued)

(58) Field of Classification Search
CPC ...... A61M 11/00; A61M 11/02; A61M 11/04;
A61M 11/041; A61M 11/042; A61M 11/044; A61M 11/06; A61M 15/0003; A61M 15/0086; A61M 15/009; A61M 15/08; A61M 16/0009; A61M 16/0012; A61M 16/0057; A61M 16/0066;
(Continued)

(56) References Cited

U.S. PATENT DOCUMENTS 2,761,055 A * 8/1956 Ike ....................... A61M 11/041
128/203.27
3,757,082 A * 9/1973 Goicoechea .......... A61M 16/16
261/DIG. 65
(Continued)

FOREIGN PATENT DOCUMENTS

CA    2689364    1/1998
DE    24 18 749    10/1975
(Continued)

*Primary Examiner* — (Jackie) Tan-Uyen T Ho
*Assistant Examiner* — Joseph D Boecker
(74) *Attorney, Agent, or Firm* — Mark David Torche; Patwrite LLC

(57) ABSTRACT

An apparatus for preparing a mixture suitable for a hyperthermal inhalational treatment of an upper portion of respiratory tract is disclosed. The apparatus includes a vertical wall defining an interior compartment, wherein a mixture of mist and vapors of an inhalant is formed. A preferably added module for a hyperthermal inhalational treatment combined with administration of pharmaceuticals and/or saline is disclosed as well.

19 Claims, 4 Drawing Sheets

(51) Int. Cl.

| | | |
|---|---|---|
| *A61M 16/08* | (2006.01) | |
| *A61M 16/10* | (2006.01) | |
| *A61M 11/06* | (2006.01) | |
| *A61M 11/04* | (2006.01) | |
| *A61M 15/00* | (2006.01) | |
| *A61M 16/06* | (2006.01) | |
| *A61M 16/04* | (2006.01) | |
| *A61M 15/08* | (2006.01) | |
| *A61M 16/14* | (2006.01) | |
| *A61M 11/00* | (2006.01) | |

(52) U.S. Cl.
CPC ........ *A61M 11/06* (2013.01); *A61M 15/0003* (2014.02); *A61M 16/0066* (2013.01); *A61M 16/049* (2014.02); *A61M 16/0666* (2013.01); *A61M 16/0816* (2013.01); *A61M 16/0875* (2013.01); *A61M 16/107* (2014.02); *A61M 16/109* (2014.02); *A61M 11/005* (2013.01); *A61M 15/08* (2013.01); *A61M 16/14* (2013.01); *A61M 16/162* (2013.01); *A61M 2202/0007* (2013.01); *A61M 2202/0468* (2013.01); *A61M 2205/07* (2013.01); *A61M 2205/3368* (2013.01); *A61M 2205/3673* (2013.01); *A61M 2205/50* (2013.01); *A61M 2210/0625* (2013.01)

(58) Field of Classification Search
CPC ................ A61M 16/10; A61M 16/104; A61M 16/1075; A61M 16/108; A61M 16/1085; A61M 16/109; A61M 16/12; A61M 16/127; A61M 16/14; A61M 16/16; A61M 2205/36; A61M 2205/362; A61K 9/0073; A61K 9/0078
USPC ............ 128/200.11, 200.14, 200.18, 200.21, 128/200.24, 203.12, 203.15–203.17, 128/203.22, 203.26, 203.27, 204.14, 128/204.17, 204.18, 204.24, 204.25; 239/135–138, 338; 261/141, 142; 514/958
See application file for complete search history.

(56) References Cited

U.S. PATENT DOCUMENTS

| | | | | |
|---|---|---|---|---|
| 3,990,441 | A * | 11/1976 | Hoyt | A61M 16/1075 128/200.18 |
| 4,036,919 | A * | 7/1977 | Komendowski | A61M 16/16 128/200.13 |
| 4,192,836 | A | 3/1980 | Bartscher | |
| 4,291,838 | A | 9/1981 | Williams | |
| 4,566,450 | A | 1/1986 | Brossman, Jr. | |
| 4,649,911 | A | 3/1987 | Knight et al. | |
| 5,267,555 | A | 12/1993 | Pajalich | |
| 5,461,695 | A | 10/1995 | Knoch | |
| 5,857,062 | A * | 1/1999 | Bergamaschi | A61M 16/16 128/203.16 |
| 2004/0060556 | A1 | 4/2004 | Halamish | |
| 2007/0256686 | A1 * | 11/2007 | Lerner | A61M 16/1075 128/200.23 |
| 2008/0223953 | A1 * | 9/2008 | Tomono | A01M 1/205 239/102.2 |
| 2008/0295831 | A1 * | 12/2008 | Svehaug | A61M 11/02 128/203.15 |
| 2009/0056712 | A1 * | 3/2009 | Cortez, Jr. | A61M 16/08 128/203.26 |
| 2010/0086449 | A1 * | 4/2010 | Delanef | A61M 16/14 422/121 |
| 2010/0258114 | A1 * | 10/2010 | Cortez, Jr. | A61M 11/005 128/200.23 |

FOREIGN PATENT DOCUMENTS

| | | | |
|---|---|---|---|
| EP | 0298389 | 1/1989 | |
| EP | 0824041 A2 * | 2/1998 | ............... A61L 9/22 |
| EP | 2018199 | 1/2009 | |
| EP | 2335761 | 6/2011 | |
| GB | 1359280 | 7/1974 | |
| GB | 2 177 006 A | 1/1987 | |
| JP | 2006 217955 A | 8/2006 | |
| JP | 2010240189 | 10/2010 | |
| JP | 2010 273701 A | 12/2010 | |
| WO | WO 96/34642 | 11/1996 | |
| WO | 00/54892 | 9/2000 | |
| WO | 2009/058032 | 5/2009 | |
| WO | 2012/026963 | 3/2012 | |

* cited by examiner

```
                    ┌─────────┐ ╭─102
                    │  START  │
                    └────┬────┘
                         │            ╭─104
                  ┌──────▼──────┐
                  │   AIRFLOW   │
                  └──────┬──────┘
                         │                          ╭─106
         ┌───────────────▼────────────────────────┐
         │  AIRFLOW CIRCULATION THROUGH INHALANT  │
         └───────────────┬────────────────────────┘
                         │                          ╭─108
         ┌───────────────▼────────────────────────┐
    ┌───▶│  HEATING WHILE CIRCULATING THROUGH INHALANT │
    │    └───────────────┬────────────────────────┘
    │                    │                          ╭─110
    │    ┌───────────────▼────────────────────────┐
 INSUFFICIENT │ MIXTURE OF INHALANT VAPORS AND MIST │◀─┐
    │    └───────────────┬────────────────────────┘  │
    │           ╭─112    │         ╭─114             │
    │         ╱       ╲  │       ╱       ╲    NO     │
    └────────╱TEMPERATURE╲ SUFFICIENT ╱ MANUAL  ╲──────┘
             ╲  CHECK   ╱──────────╲ ACTIVATION ╱
              ╲       ╱             ╲         ╱
                                      YES
                                       │              ╭─116
              ┌────────────────────────▼─────────────┐
              │       ACTIVATING COMPRESSOR          │
              └────────────────┬─────────────────────┘
                               │                      ╭─118
              ┌────────────────▼─────────────────────┐
              │ NEBULIZING PHARMACEUTICALS SOLUTION/SALINE │
              └────────────────┬─────────────────────┘
                               │                      ╭─120
                      ┌────────▼────────┐
                      │    PREMIXING    │
                      └────────┬────────┘
                               │         ╭─122
                          ┌────▼────┐
                          │   END   │
                          └─────────┘
```

Fig. 4

SYSTEMS AND METHODS OF PREPARING A CONTROLLED MIXTURE FOR HYPERTHERMAL TREATMENT

TECHNICAL FIELD

In general, the present invention pertains to the arts of medical devices. In particular, the invention relates to systems and methods of preparing a mixture suitable for hyperthermal treatment, preferably combined with administration of pharmaceuticals.

BACKGROUND ART

It is believed that the pertinent state-of-the-art is represented by: U.S. Pat. Nos. 4,649,911, 3,387,607, 4,110,419, 4,303,601, 5,769,071, 5,267,555 7,228,859 and 7,523,751; French patent/s or patent application/s Ser. Nos 4029781, 661696, 19541483 and 4109269; French patent Ser. No. 2543442; GB patent 1359280; Japanese patent publications Ser. No. 2010240189, 5345027 and 5000162; Chinese patents/utility models 2083936U, 2146252Y, 201020125Y 2822668Y and 2535068Y; Canadian patent application CA2689364 as well as by international patent applications having publication No. WO0054892 and WO2008036801.

SUMMARY OF THE INVENTION

There is provided in accordance with embodiments of the present invention systems and methods for hyperthermal treatment combined with administration of pharmaceuticals, comprising a blower that is powered and activated by electrical power supply block and control system. The blower draws an inflow of air, filtered by an air filter, providing a pressurized airflow into the inhalation module. The low pressure airflow into the inhalation module, encircles an interior compartment from the outside, in-between cylindrical walls, defining the interior compartment, and exterior housing 13 of inhalation module.

The pressurized airflow is thereafter forced to overflow underneath cylindrical walls, into the interior compartment. The level of inhalant in the bottom of the exterior housing of the inhalation module, is somewhat higher than the bottom edge of cylindrical walls, thereby the low pressure airflow is forced to circulate through the solution of inhalant, in the vicinity of an electrical heating element.

The vapors of inhalant produced by the electrical heating element, as well as the mist of inhalant produced by a forced circulation of the pressurized airflow through the solution of inhalant underneath the bottom edge of the cylindrical walls, are supplied into the interior compartment from the bottom, rise upwards within compartment and pass via a grating, providing for electrical grounding of the static charge from the mix of vapors and mist of the inhalant.

An air pressure compressor, which is powered and activated by the electrical power supply block and control system, is optionally employed for providing a higher pressure airflow into pharmaceuticals nebulizer module. The pharmaceuticals nebulizer module, is any type of a nondestructive nebulizer, which typically does not employ heating, ultrasonic or vibratory effect or another destructive mechanical or other effect on pharmaceuticals solution or saline. The pharmaceuticals nebulizer module is preferably a Venturi nebulizer, known in the art. The pharmaceuticals nebulizer module contains pharmaceuticals solution or saline.

The pharmaceuticals nebulizer module produces aerosols of nebulized pharmaceuticals solution, which is thereafter supplied into the mixing module. In the mixing module, aerosols of nebulized pharmaceuticals solution are mixed with vapors and mist of the inhalant. The mixture of aerosols of nebulized pharmaceuticals solution with vapors and mist of the inhalant is supplied from mixing module via a flexible hose into a handpiece and discharged from nozzles therein.

Optionally, the electric engine powering the blower also powers the higher pressure compressor. In such case a coupling mechanism is employed to controllably convey the rotational torque to the compressor.

DESCRIPTION OF THE DRAWINGS

The present invention will be understood and appreciated more comprehensively from the following detailed description taken in conjunction with the appended drawings in which:

FIG. 4 is a high-level flowchart diagram, visualizing an embodiment of the method of the invention, of preparing a mixture suitable for hyperthermal treatment and administration of pharmaceuticals;

DETAILED DESCRIPTION OF EMBODIMENTS

Figure 1:
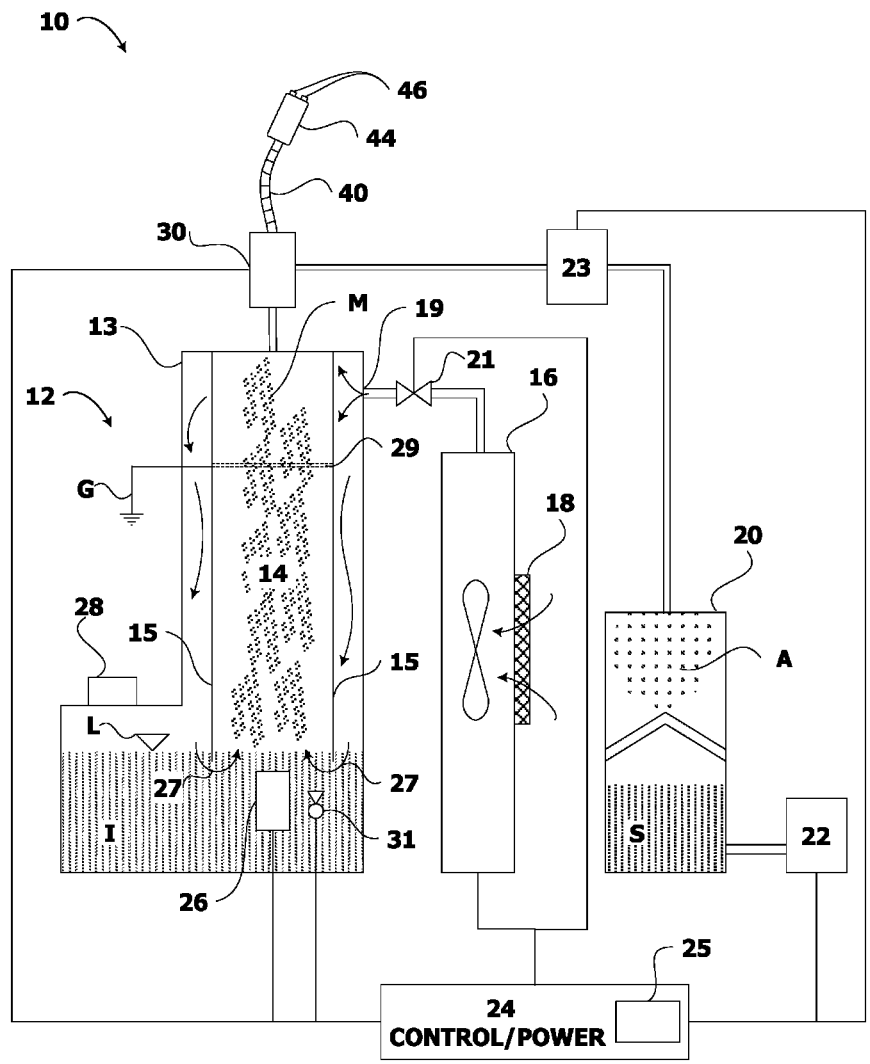
FIG. 1 is a schematic cross-sectional diagram of an embodiment of the system of the invention for preparing a mixture suitable for hyperthermal treatment and administration of pharmaceuticals.

In accordance with some embodiments of the present invent, reference is now made to FIG. 1, showing system 10, for preparing a mixture suitable for hyperthermal treatment and/or administration of pharmaceuticals. System 10 for preparing a mixture suitable for hyperthermal treatment, optionally combined with administration of pharmaceuticals, is preferably employed for inhalational treatment; however other treatment indications, such as oral, topical, ontological, rectal, vaginal, are explicitly emphasized. System 10 is particularly adapted for preparing a mixture suitable for hyperthermal inhalational treatment of optionally combined with administration of pharmaceuticals into the upper respiratory tract. System 10 comprises inhalation module 12, blower module 16, pharmaceuticals nebulizer module 20 and mixing module 30 as well as electrical power supply block and control system 24, powering the aforesaid modules and controlling the operation thereof. Power supply block and control system 24 preferably comprises a user interface 25, typically including a display and operation buttons.

Inhalation and Blower Modules

System 10 comprises inhalation module 12, which is encompassed within exterior housing 13. Inhalation module 12 further comprises vertical walls 15. Walls 15 extend within exterior housing 13, essentially vertically, typically from the top portion of housing 13 but not to the bottom of housing 13. Consequently, at the bottom, walls 15 terminate with at least one butt-end, which is disposed at a predetermined distance from the bottom of housing 13. Walls 15 define interior compartment 14 of inhalation module 12, where the inhalant vapors and mist are formed, as will be elaborated infra.

Walls 15 are typically disposed at some distance, interiorly to exterior housing 13 of inhalation module 12; thereby allowing circulation of incoming airflow in-between walls 15 and exterior housing 13. In some preferred embodiments walls 15 embody an essentially cylindrical shape, thereby facilitating a more homogenous or laminar circulation of airflow in-between walls 15 and exterior housing 13, essentially within the direction of arrows, as shown in FIG. 1. It should be noted however that the preferred instance of an essentially cylindrically shaped walls 15 is merely exemplary and other shapes of walls 15 are as well possible and contemplated by this disclosure.

System 10 further comprises blower module 16. Blower module 16 is adapted to generate airflow of a relatively lower pressure, in a continuous manner. Blower module 16 is connected to, powered and actuated by electrical power supply block and control system 24 of system 10. Blower module 16 is typically a type of fan-like device, known in the art. Blower module 16 is typically furnished with air filter 18, adapted to filter the air drawn into blower module 16. Ambient air is drawn into blower module 16, essentially within the direction of arrows, as shown in FIG. 1.

Thereafter the airflow of a relatively lower pressure generated by blower module 16 is conducted into inhalation module 12, essentially within the direction of arrows, as shown in FIG. 1. Inlet 19, for the incoming airflow, conducted from blower module 16, is preferably located at the top portion of inhalation module 12. Inlet 19 is typically located in-between walls 15 and exterior housing 13 of inhalation module 12; whereby the airflow incoming into inhalation module 12 from blower module 16 is optimally distributed in the space in-between walls 15 and exterior housing 13, essentially within the direction of arrows, as shown in FIG. 1. Optionally baffle 21 is disposed in-between from blower module 16 and inlet 19 for the incoming airflow. Baffle 21 is connected, powered and controlled by electrical power supply block and control system 24.

Inhalation module 12 contains liquid and/or inhalant I. Inhalant I is typically water or an aqueous solution. Inhalant I is typically contained within the bottom portion exterior housing 13; however a particularly dedicated receptacle (not shown) is optionally provided at the bottom portion exterior housing 13 to accommodate liquid and/or inhalant I at the bottom portion exterior housing 13.

As previously noted, system 10 is preferably employed for inhalational treatment; however since other treatment indications, such as topical, ontological, rectal, vaginal, are existent—the terms inhalation, inhalation module and/or inhalant are not to be construed as entailing an implementation for inhalational treatment but rather as terms describing a mixture suitable for hyperthermal treatment.

Among various implementations of system 10 of the present invention, inhalational treatment is merely a typical or preferable medical indication therefor; whereas numerous other indications, non-related to inhalation, such as topical and ontological, are existent and contemplated in the scope of the present invention. Therefore the use of the term terms inhalation and/or inhalant is intended to describe the physical output of system 10, comprising a mixture of vapors and mist—without signifying the implementation of system 10 in a particular medical indication.

The level of inhalant I in inhalation module 12 is denoted as L. Inlet 28 is dedicated for filling inhalant I into inhalation module 12. Preferably, inlet 28 is furnished with a mechanism which limits the supply of inhalant I into inhalation module 12 above the predetermined level L. Instances of such mechanisms that limit the supply of inhalant I into inhalation module 12 above the predetermined level L inter alia include inverted-reservoir type devices, such as inverted-reservoir device disclosed in U.S. Pat. No. 7,523,751.

The predetermined level L of inhalant I in inhalation module 12, which is typically maintained rater constant by the aforementioned mechanism, is preferably somewhat higher than the level of the butt-end at the bottom of walls 15, defining interior compartment 14 of inhalation module 12. Consequently, the airflow incoming into inhalation module 12 from blower module 16 is forced to overflow underneath walls 15 and through inhalant I, within the direction of arrows 27, before entering into interior compartment 14 of inhalation module 12; whereby mist M of inhalant I is produced within interior compartment 14 inter alia due to the bubbling of the airflow through inhalant I underneath walls 15, within the direction of arrows 27.

Inhalation module 12 further comprises electrical heating element 26. Electrical heating element 26 is connected to, powered and actuated by electrical power supply block and control system 24 of system 10. Electrical heating element 26 is typically disposed within inhalant I, electrically insulated from the latter. Electrical heating element 26 is typically disposed somewhat concentrically to interior compartment 14 and within the vicinity of the bottom of walls 15. Consequently the airflow that is forced to overflow underneath walls 15 through inhalant I, within the direction of arrows 27, circulates within vicinity of electrical heating element 26 and sweeps away the bubbles of vapor of inhalant I produced on the surface of the latter within the current thereof.

Moreover, the aforementioned circulation of the airflow underneath walls 15 into interior compartment 14, within the direction of arrows 27, facilitates an enhanced circulation of liquid inhalant I about heating element 26 (not shown). The enhanced circulation of liquid inhalant I around heating element 26 facilitates an enhanced convective cooling of the later; whereby a more powerful electrical heating element, with a higher production of vapor, can be employed, without the concern of overheating, which might have been occurred in a non-circulating or static environment of inhalant I.

In light of the foregoing, the airflow into interior compartment 14 after the aforementioned circulation underneath walls 15 through inhalant I and within vicinity of electrical heating element 26 is characterized by a relatively high content of mist of inhalant I as well as by a relatively high content of vapor of inhalant I, forming a rich mixture of mist and vapor of inhalant I, denoted as M. Mixture M of mist and vapor of inhalant I raises within interior compartment 14, essentially as shown in FIG. 1.

As it was surprisingly discovered by the developers of this invention that mixture M of mist and vapor of inhalant I, raising within interior compartment 14, is capable of exhibiting a substantial difference of potentials, relatively to the grounding or ambient air, due to a static electrical charge or a conduction of electrical current from an insufficiently electrically insulated heating element 26. Therefore and in order to prevent an electrocution of a patient, grating 29 is disposed across the essentially the entire cross-section of interior compartment 14 of inhalation module 12, for discharging an excessive difference of potentials of mixture M, relatively to the ground or ambient air. Accordingly, grating 29 is coupled to a grounding source, as schematically shown in FIG. 1, for achieving the discharging of mixture M. In favor of these who shall engage in an experimentation guided by this disclosure, it is disclosed that the developers of this invention have empirically discovered that a grating with a substantially spaced apart or non dense arrangement of inter-crossing members, which essentially neither capture particles of the mist from mixture M nor condense the vapors from mixture M, can be used in order to achieve an efficient electrical discharging and grounding of mixture M. From an outlet at the top of interior compartment 14, mixture M, preferably after grounding by grating 29, is conducted from of inhalation module 12 into mixing module 30.

Typically, a thermal sensor 31 is disposed in inhalation module 12, preferably within vicinity or adjacently to electrical heating element 26. Thermal sensor 31 is connected, powered and controlled by electrical power supply block and control system 24. Thermal sensor 31 is employed to monitor and control the operation of electrical heating element 26 and/or for shutting the power to electrical heating element 26 off, upon overheating of the latter.

Pharmaceuticals Nebulizer Module

System 10 comprises pharmaceuticals nebulizer module 20. Pharmaceuticals nebulizer module 20 is adapted to produce fine aerosols A of nebulized pharmaceuticals solution or saline S, wherein the former is thereafter supplied into mixing module 30. Pharmaceuticals nebulizer module 20 is typically contains pharmaceuticals solution or saline S; however in some instances pharmaceuticals solution or saline S is contained in a separate reservoir and supplied into the nebulizer module (not shown). It should be acknowledged that system 10 optionally comprises a plurality of different pharmaceuticals nebulizer modules 20, optionally preloaded with different pharmaceuticals solutions or different types of saline S.

Pharmaceuticals nebulizer module 20 optionally comprises air pressure compressor 22. Air pressure compressor 22 is connected to, powered and actuated by electrical power supply block and control system 24 of system 10. Air pressure compressor 22 is any type of compressor known in the art. Air pressure compressor 22 is typically furnished with air filter (not shown), adapted to filter the air drawn by compressor 22. Ambient air is drawn into air pressure compressor 22 and thereafter conducted into pharmaceuticals nebulizer module 20, essentially as shown in FIG. 1.

In pharmaceuticals nebulizer module 20, pharmaceuticals solution or saline S is nebulized into fine aerosols A, which are further forced by the pressurized air from air compressor 22 into the mixing module 30. The pharmaceuticals nebulizer module, is any type of a nondestructive nebulizer. A nondestructive nebulizer as referred to herein is any type of nebulizer that does not have a harmful affect on the quality of pharmaceuticals solution or saline S. A nondestructive nebulizer, as referred to herein, is any type of nebulizer that does not employ excessive heating, powerful ultrasonic or vibratory effect or another destructive mechanical or other effect, which may be harmful to the composition of a pharmaceuticals solution and/or may cause a sedimentation or precipitation of the substances dissolved therein, e.g. with a saline. It should be acknowledged, however, that the nature of the nebulizer, being a destructive or nondestructive, is determined by the type of pharmaceuticals solution or saline S. Thus for instance an ultrasonic nebulizer can be destructive for pharmaceuticals solution containing protein or other sensitive molecules; whereas the very same ultrasonic nebulizer can be nondestructive for a saline.

The pharmaceuticals nebulizer module is preferably comprises a Venturi-type of nebulizer, known in the art. A venturi-type of nebulizer is disclosed in US2004/60556 entitled DOWNDRAFT NEBULIZER and elsewhere. In the instances of a Venturi-type of nebulizer, the air pressure itself achieves the nebulization of solution or saline S into fine aerosols A.

Optionally, the blower of blower module 16 as well as air compressor 22 of nebulizer module 20 are driven by a shaft of a single electric engine. In such case a coupling means is preferably employed to controllably operate air compressor 22 of nebulizer module 20 apart the blower of blower module 16.

Optionally, a baffle and/or sensors sub-module 23 is disposed in-between pharmaceuticals nebulizer module 20 and mixing module 30. Baffle and/or sensors sub-module 23 is connected, powered and controlled by electrical power supply block and control system 24. Baffle and/or sensors sub-module 23 is employed to monitor and control the aerosols A flow into mixing module 30.

Mixing Module

System 10 comprises mixing module 30. To illustrate a preferred embodiment of mixing module 30, reference is now made to FIGS. 2 and 3. Mixing module 30 receives mixture M from inhalation module 12 and aerosols A from pharmaceuticals nebulizer module 20 and mixes the former with the latter into mixture M+A, suitable for hyperthermal treatment with mist and vapor of inhalant I combined with administration of nebulized pharmaceuticals solution or saline S. A unidirectional check-valve (not shown) is typically disposed in-between mixing module 30 and inhalation module 12, to prevent backward flow pharmaceuticals solution or saline S from mixing module 30 to inhalation module 12. Mixing module 30 preferably employs a Venturi-tube configuration. Mixture M is supplied from inhalation module 12 into the portion of the Venturi-tube having a wider cross-section. With advancement into mixing module 30 the cross-section of the Venturi-tube narrows, whereby the flow increases and a relatively negative pressure is formed.

Figure 2:
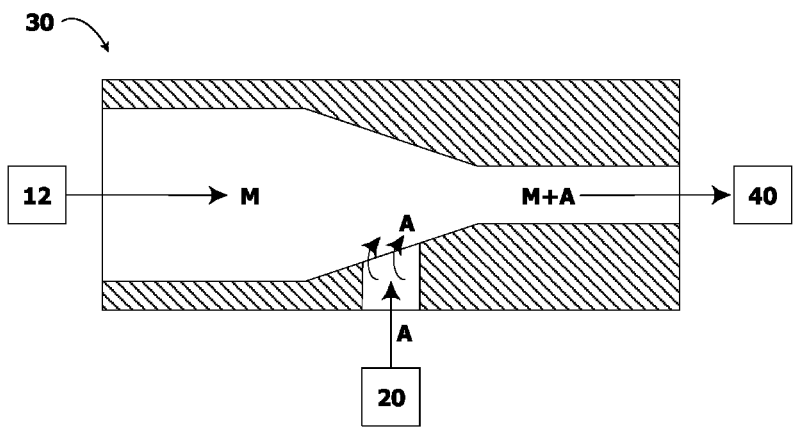
FIG. 2 is a schematic cross-sectional diagram of an embodiment of the mixing module of the invention.
Figure 3:
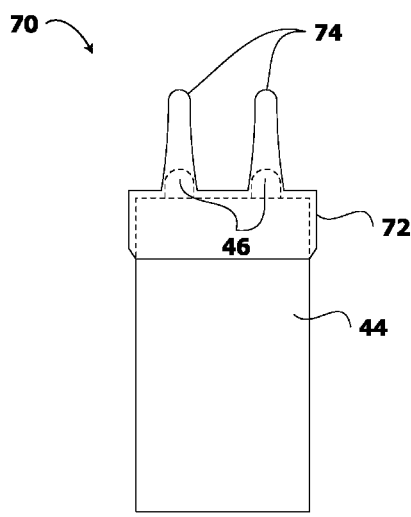
FIG. 3 is a schematic diagram of an embodiment of the handpiece of the invention.

Aerosols A are supplied from pharmaceuticals nebulizer module 20 into the portion of mixing module 30 where the cross-section of the Venturi-tube is narrower, whereby aerosols A are drawn by the relatively negative pressure and forcefully sucked into the flow of mixture M, essentially within the direction of arrows, as shown in FIG. 2. Consequently an essentially homogenous master mixture M+A, of mixture M and aerosols A, suitable for hyperthermal treatment with mist and vapor of inhalant I combined with administration of nebulized pharmaceuticals solution or saline S, is formed and thereafter supplied into hose 40.

Hose 40 is preferably a corrugated type of hose, capable of substantial flexibility. Master mixture M+A is further conducted by hose 40 into handpiece 44. Handpiece 44 is preferably thermally insulating master mixture M+A from the exterior surface thereof; thereby allowing to conveniently grip handpiece 44 during the administration of master mixture M+A. Handpiece 44 terminates with nozzles 46 which are adapted to be positioned vis-à-vis the nostrils of a patent; thereby supplying master mixture M+A directly into the upper respiratory tract.

Optionally, mixing module 30 comprises a baffle and/or sensors connected, powered and controlled by electrical power supply block and control system 24. Baffle and/or sensors of mixing module 30 are employed to monitor and control the outflow of master mixture M+A into hose 40 and/or mixing ratio between aerosols A and mixture M To illustrate a preferred embodiment of handpiece 44, reference is now made to FIG. 3. Optionally, handpiece 44 is furnished with extension add-on 70. Extension add-on 70 comprises covering portion 72 and a couple of nasal extensions 74. Covering portion 72 of add-on 70 is adapted to conform to the anterior portion of handpiece 44, adjoining the bases of nasal extensions 74 to nozzles 46 of handpiece 44. Nasal extensions 74 are adapted to be inserted into nostrils; thereby upon adjoining the bases of nasal extensions 74 to nozzles 46, extensions 74 conduct master mixture M+A directly into deeper superior portion of nasal cavity.

Method of the Invention

To visualize an embodiment of the method of the invention, of preparing a mixture suitable for hyperthermal treatment and administration of pharmaceuticals, reference is now made to FIG. 4. The process of preparing a mixture suitable for hyperthermal treatment and administration of pharmaceuticals commences at step 102, with actuation of the means for airflow production. Upon actuation of the means for airflow production at step 102, an airflow is produced at step 104.

Thereafter, at step 106, the airflow produced at step 104, is forced to circulate through inhalant. Additionally, at step 108, the inhalant is heated, while the airflow produced at step 104 is forced to circulate through the inhalant. Consequently a mixture of mist of the inhalant and vapors of the inhalant, suitable for hyperthermal treatment, is produced at step 110. The mere mixture of mist and vapors of the inhalant, produced at step 110, is optionally used for solely a hyperthermal treatment, without administration of pharmaceuticals; whereby the method is optionally terminates at step 110.

Optionally, the temperature mixture of mist and vapors of the inhalant, produced at step 110, is monitored during step 112. If the temperature has not reached a predetermined threshold, the heating of the inhalant at step 108 is repeated or intensified. If the temperature has reached a predetermined threshold, the method proceeds to step 114. Optionally, if at step 114, a manual activation is received, the method proceeds to step 116; whereas if at step 114, a manual activation is not received, the method returns to step 110 and a mixture of mist and vapors of the inhalant is constantly produced. Optionally there is possibility to manually suppress steps 112 and/or 114 and forcefully proceed to step 116.

At step 116 an air compressor is optionally activated and pressurized air is produced. Concomitantly or thereafter a pharmaceuticals solution and/or saline is nebulized into final aerosols, at step 118. The aerosols of nebulized pharmaceuticals solution and/or saline produced at step 118 are then premixed during step 120 with the mixture of mist and vapors of the inhalant, produced at step 110.

The method of the invention ends at step 122 with production of the master-mixture of aerosols of nebulized pharmaceuticals solution/saline, from step 118, and the mixture of mist and vapors of the inhalant, at step 110.

Figure 5A:
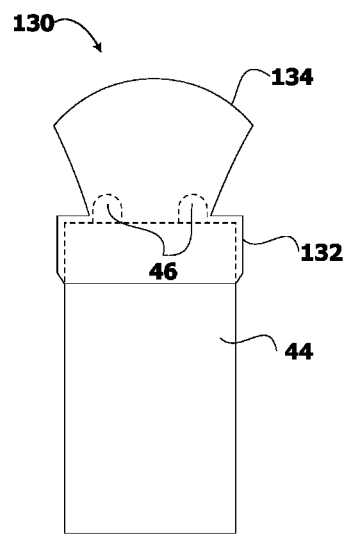
FIGS. 5A to 5C are schematic diagram of embodiments of the handpiece of the invention.

To illustrate another preferred embodiment of handpiece 44, reference is now made to FIG. 5A. Optionally, handpiece 44 is furnished with extension add-on 130. Extension add-on 130 comprises covering portion 132 and singular widespread nozzle 134. Covering portion 132 of add-on 130 is adapted to conform to the anterior portion of handpiece 44, adjoining the bases of singular widespread nozzle 134 to nozzles 46 of handpiece 44. Widespread nozzle 134 is adapted for oral inhalational administration and/or topical application of master mixture M+A; thereby upon adjoining the bases of covering portion 132 to nozzles 46, widespread nozzle 134 conducts mixture M+A directly into the oral cavity or onto the site of topical application.

Figure 5B:
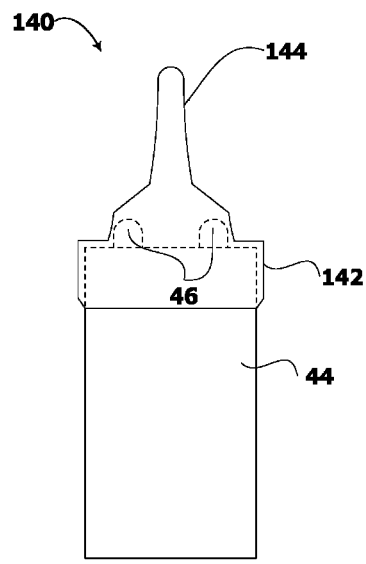

To illustrate another preferred embodiment of handpiece 44, reference is now made to FIG. 5B. Optionally, handpiece 44 is furnished with extension add-on 140. Extension add-on 140 comprises covering portion 142 and singular centric extension 144. Covering portion 132 of add-on 130 is adapted to conform to the anterior portion of handpiece 44, adjoining the bases of centric extension 144 to nozzles 46 of handpiece 44. Centric extension 144 is intended for ontological, rectal and/or vaginal applications and adapted to be inserted into an orifice of a patient; thereby upon adjoining the bas of centric extension 144 to nozzles 46, centric extension 144 conducts master mixture M+A directly into deeper into an orifice of a patient.

Figure 5C:
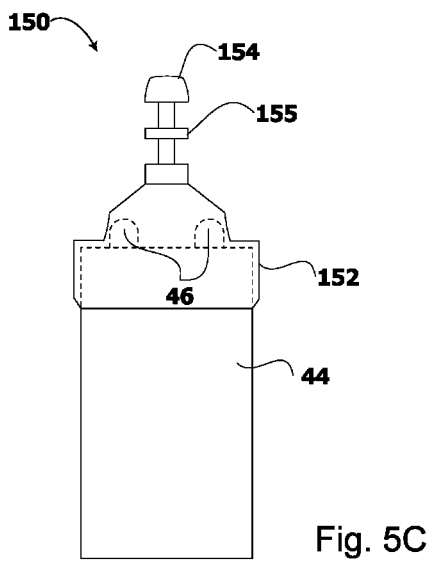

To illustrate another preferred embodiment of handpiece 44, reference is now made to FIG. 5C. Optionally, handpiece 44 is furnished with extension add-on 150. Extension add-on 150 comprises covering portion 152 and miscellaneous connector 154. Covering portion 152 of add-on 150 is adapted to conform to the anterior portion of handpiece 44, adjoining the bases of miscellaneous connector 154 to nozzles 46 of handpiece 44. Centric extension 154 is intended for connection to inhalators, respiratory machines and/or general anesthesia systems; thereby upon adjoining the bases of miscellaneous connector 154 to nozzles 46, miscellaneous connector 154 conducts master mixture M+A into an appliance. Miscellaneous connector 154 optionally includes rib 155, for firm connection with compatible connection or inlet of an appliance.

The invention claimed is:

1. A system for preparing a mixture; suitable for a hyperthermal inhalational treatment of and administration of pharmaceuticals into an upper portion of a respiratory tract, said system comprising:
   (a) an inhalation module, said inhalation module comprises:
      (i) an exterior housing encompassing said inhalation module;
      (ii) at least one substantially vertical wall disposed within said housing, wherein the distance from a bottom portion of said wall to a bottom of said housing is greater than zero;
      (iii) an interior compartment within said housing; defined by said at least one substantially vertical wall;
      (iv) an inhalant contained within said housing; wherein said bottom portion of said wall is disposed lower than an upper level of said inhalant;
      (v) an air flow inlet, disposed exteriorly to said interior compartment;
      (vi) an inhalant inlet, for supplying said inhalant into said housing;
      (vii) an outlet, disposed within said interior compartment; and
      (viii) an electrical heating element, configured to heat said inhalant;
   (b) a blower module, configured to generate an airflow of a low pressure; said blower module is connected to said inhalation module and supplies said airflow in a continuous manner thereto;
   (c) a nebulizer module, configured to produce aerosols of at least one member selected from the group consisting of: a nebulized pharmaceutical solution and nebulized saline; said nebulizer module comprises:
      (i) an air pressure compressor, configured to generate a pressurized air of a higher pressure than the low pressure of said blower module;
      (ii) a non-destructive nebulizer;

(iii) at least one member selected from the group consisting of: a pharmaceutical solution and saline;

(d) a mixing module, said mixing module is connected to said inhalation module and said nebulizer module, said mixing module comprises:

(i) a flexible hose, to conduct a mixture produced in said mixing module;

(ii) a handpiece, at a terminal of said hose;

(iii) at least one nozzle, at the an anterior of said handpiece;

wherein said system is characterized by that:

(e) said electrical heating element is disposed essentially concentrically relatively to said interior compartment, and (f) said electrical heating element is disposed adjacently to said bottom portion of said wall;

(g) said airflow generated by said blower is configured to flow into said interior compartment from said airflow inlet of said housing, underneath said bottom portion of said wall and concomitantly through said inhalant, adjacently to said electrical heating element, wherein:

(i) said flow underneath said bottom portion of said wall and concomitantly through said inhalant, adjacently to said electrical heating element, is configured to form intensive circulation of said inhalant and concomitantly intensive circulation of said airflow adjacently to said electrical heating element; whereby said system is configured to sustain enhanced convective cooling of said electrical heating element and surplus production of vapors of said inhalant, by said intensive circulations of said inhalant and said airflow adjacently to electrical heating element;

(ii) said flow underneath said bottom portion of said wall and concomitantly through said inhalant, adjacently to said electric heating element, is configured to mechanically form and enrich said airflow with heated aerosols mist of said inhalant;

with a proviso that said electrical heating element is a singular heating element and not multiple tilted heating elements.

2. The system for preparing a mixture, as set forth in claim 1, wherein said inhalant inlet comprises a mechanism comprising a limiter which is configured to limit a supply of said inhalant into said housing above a predetermined level.

3. The system for preparing a mixture, as set forth in claim 2, wherein said predetermined level of said inhalant is higher than a level of said bottom portion of said wall.

4. The system for preparing a mixture, as set forth in claim 1, wherein said airflow incoming into said inhalation module is forced to overflow underneath said walls and through said inhalant before entering into said interior compartment; whereby a mist of said inhalant is produced within said interior compartment.

5. The system for preparing a mixture, as set forth in claim 1, wherein a circulation of said airflow underneath said wall is adapted to sustain an enhanced convective cooling of a more powerful electrical heating element having higher vapor production.

6. An apparatus for preparing a controlled mixture of vapors and mist, suitable for at least a hyperthermal inhalational treatment of an upper portion of a respiratory tract, said apparatus comprising:

(a) an exterior housing encompassing said apparatus;

(b) at least one substantially vertical wall disposed within said housing, wherein a distance from a bottom portion of said wall to a bottom of said housing is greater than zero;

(c) an interior compartment within said housing, defined by said at least one substantially vertical wall;

(d) an inhalant contained within said housing, wherein said bottom portion of said wall is disposed lower than an upper level of said inhalant;

(e) an air flow inlet; disposed exteriorly to said interior compartment;

(f) an inhalant inlet, for supplying said inhalant into said housing;

(g) an outlet, disposed within said interior compartment; and (h) an electrical heating element, configured to heat said inhalant;

(i) a blower, configured to generate an airflow of a low pressure at said air flow inlet;

(j) a flexible hose, configured to conduct a mixture produced in said interior compartment;

(k) a handpiece, at a terminal portion of said flexible hose;

(l) at least one nozzle, at an anterior portion of said handpiece;

wherein said apparatus is characterized by that:

(m) said electrical heating element is disposed essentially concentrically relatively to said interior compartment, and (n) said electrical heating element is disposed adjacently to said bottom portion of said wall;

(o) said airflow generated by said blower is configured to flow into said interior compartment from said airflow inlet of said housing, underneath said bottom portion of said wall and concomitantly through said inhalant, adjacently to said electrical heating element, wherein:

(i) said flow underneath said bottom portion of said wall and concomitantly through said inhalant, adjacently to said electrical heating element, is configured to form intensive circulation of said inhalant and concomitantly intensive circulation of said airflow adjacently to said electrical heating element; whereby said system is configured to sustain enhanced convective cooling of said electrical heating element and surplus production of vapors of said inhalant, by said intensive circulations of said inhalant and said airflow adjacently to electrical heating element;

(ii) said flow underneath said bottom portion of said wall and concomitant through said inhalant adjacently to said electrical heating element, is configured to mechanically form and enrich said airflow with heated aerosols mist of said inhalant;

with a proviso that said electrical heating element is a singular heating element and not multiple tilted heating elements.

7. The apparatus for preparing a mixture, as set forth in claim 6 further comprises:

(a) a nebulizer module, configured to produce aerosols of at least one member selected from the group consisting of: a nebulized pharmaceutical solution and nebulized saline; said at least one nebulizer module comprises:

(i) a non-destructive nebulizer;

(ii) at least one member selected from the group consisting of: said pharmaceutical solution and said saline;

(b) a mixing module, said mixing module is connected to said apparatus and said nebulizer module and mixes the product of said apparatus with the product of said nebulizer module.

8. The apparatus for preparing a mixture, as set forth in claim 7, wherein said at least one nebulizer module further comprises an air pressure compressor, capable of generating a pressurized air.

9. The apparatus for preparing a mixture, as set forth in claim 6, wherein said wall is disposed interiorly to said housing of said apparatus; thereby allowing a circulation of airflow in-between said wall and said housing.

10. The apparatus for preparing a mixture, as set forth in claim 6, wherein said inhalant is at least one selected from the group consisting of: water and a substantially aqueous solution.

11. The apparatus for preparing a mixture, as set forth in claim 6, wherein said inhalant inlet comprises a mechanism comprising a limiter which is configured to limit a supply of said inhalant into said housing above a predetermined level.

12. The apparatus for preparing a mixture, as set forth in claim 6, comprising a mechanism configured to limit a supply of said inhalant into said housing above a predetermined level, wherein said mechanism comprising an inverted-reservoir.

13. The apparatus for preparing a mixture, as set forth in claim 11, wherein said predetermined level of said inhalant is higher than a level of said bottom portion of said wall.

14. The apparatus for preparing a mixture, as set forth in claim 6, wherein said airflow is forced to overflow underneath said walls and through said inhalant before entering into said interior compartment; whereby a mist of said inhalant is produced within said interior compartment.

15. The apparatus for preparing a mixture, as set forth in claim 6, wherein said intensive circulation of said airflow and said inhalant adjacently to said electrical heating element underneath said wall sustaining said enhanced convective cooling of said electrical heating element; is further configured to incorporate a powerful electrical heating element characterized by said surplus vapor production due to said intensive circulations of said inhalant and said airflow adjacently to said electrical heating element.

16. The apparatus for preparing a mixture, as set forth in claim 6, further comprising a grating disposed across an essentially entire cross-section of said interior compartment, for discharging an excessive difference of potentials therefrom.

17. The apparatus for preparing a mixture, as set forth in claim 7, wherein said non-destructive nebulizer is a Venturi-type of nebulizer.

18. The apparatus for preparing a mixture, as set forth in claim 8, wherein said pressure of said airflow generated by said blower is lower relatively to an air pressure generated by said compressor.

19. The apparatus for preparing a mixture, as set forth in claim 7, wherein said mixing module employs a Venturi-tube configuration.

* * * * *